United States Patent [19]

Scheithauer et al.

[11] Patent Number: 4,594,230

[45] Date of Patent: Jun. 10, 1986

[54] RECOVERY OF COBALT

[75] Inventors: Richard A. Scheithauer; Michael J. Miller; Clarence D. Vanderpool, all of Towanda, Pa.

[73] Assignee: GTE Products Corporation, Stamford, Conn.

[21] Appl. No.: 697,661

[22] Filed: Feb. 4, 1985

[51] Int. Cl.$^4$ .............................................. C01G 51/00
[52] U.S. Cl. .................................... 423/140; 423/55; 423/142; 423/150; 423/341; 423/415 R; 423/492; 423/493; 423/592; 423/606; 423/607; 423/658.5; 75/101 R; 75/108; 75/119; 75/121; 556/147; 556/62
[58] Field of Search ............... 423/140, 55, 142, 150, 423/341, 415 R, 658.5, 492, 493, 606, 607, 592; 75/108, 119, 121, 101 R; 260/429 R, 439 R

[56] References Cited

U.S. PATENT DOCUMENTS

| | | | |
|---|---|---|---|
| 3,186,829 | 6/1965 | Landgraf | 75/119 |
| 3,190,748 | 6/1965 | Landgraf | 75/119 |
| 3,511,654 | 5/1970 | Goni | 75/119 |
| 3,803,191 | 4/1974 | Ehrreich et al. | 260/439 R |
| 3,840,469 | 10/1974 | Hobbs, Jr. et al. | 260/439 R |

Primary Examiner—John Doll
Assistant Examiner—Robert L. Stoll
Attorney, Agent, or Firm—Donald R. Castle

[57] ABSTRACT

A process is disclosed for recovering cobalt in a relatively pure form from an impure cobalt bearing material. The process involves digesting the material in hydrochloric acid to form a solution essentially all of the cobalt and some impurities and insoluble material containing the remainder of the impurities, separating the solution from the insolubles, adding an oxalate producing compound in an amount sufficient to subsequently convert essentially all of the cobalt to cobalt oxalate to the solution, adjusting the pH of the oxalate treated solution to from about 1.5 to about 2.0 with a base to precipitate the cobalt, and finally separating the precipitate from the resulting mother liquor.

7 Claims, No Drawings

RECOVERY OF COBALT

FIELD OF THE INVENTION

This invention relates to a process for recovery of cobalt from impure cobalt bearing material. More particularly, it relates to a process for recovery of cobalt from impure cobalt bearing material by precipitation of cobalt oxalate from hydrochloric acid solution.

BACKGROUND OF THE INVENTION

Cobalt is recovered from a variety of materials such as scrap cemented carbides by conversion to the hexammine cobalt (III) chloride or by digestion in hydrochloric acid followed by conversion to the hexamminecobalt (III) chloride. This process is disclosed in U.S. Pat. No. 4,218,240.

However, materials such as stellites which are a class of alloys used as hard-facing material for tools and which can contain up to about 65% cobalt with varying amounts of chromium, nickel, iron, tungsten, and silicon and are therefore oxidation resistant materials by virtue of their chromium content, do not lend themselves to any simple method of recovering cobalt.

Direct conversion to hexamminecobalt (III) chloride is not possible with stellites due to their resistance to oxidation.

Conversion of the chloride mixture obtained from the hydrochloric acid digestion of the stellite material to hexammmine cobalt (III) chloride has also proved unsuccessful. At the pH necessary for converting cobalt chloride to the hexammine cobalt (III) chloride that is a pH from about 9.0 to about 9.7, both chromium and iron precipitate and poor yields result, presumably because the cobalt is trapped in the precipitate and is not oxidized. Removal of the iron and chromium by adjusting the pH of the chloride mixture to about 3.5 and filtering has also proved unsuccessful. Cobalt is either co-precipitating with iron and chromium or is being occluded resulting in the loss of cobalt during this step.

A process in which cobalt can be recovered from impure material including stellites would be an advancement in the art.

SUMMARY OF THE INVENTION

In accordance with one aspect of this invention, there is provided a process for recovering cobalt in a relatively pure form from an impure cobalt bearing material. The process involves digesting the material in hydrochloric acid to form a solution containing essentially all of the cobalt and some impurities and insoluble material containing the remainder of the impurities and separating the solution from the insolubles. An oxalate producing compound is added to the resulting solution in an amount sufficient to subsequently convert essentially all of the cobalt to cobalt oxalate. The pH is then adjusted to from about 1.5 to about 2.0 with a base to precipated the cobalt. The precipitate is then separated from the resulting mother liquor.

DETAILED DESCRIPTION OF THE INVENTION

For a better understanding of the present invention, together with other and further objects, advantages, and capabilities thereof, reference is made to the following disclosure and appended claims in connection with the foregoing description of some of the aspects of the invention.

This invention relates to a process for recovering relatively pure cobalt by precipitation of cobalt oxalate from hydrochloric acid solution.

Hydrochloric Acid Digestion of the Cobalt Bearing Material.

The starting material can be essentially any material containing cobalt such as the cobalt alloys used for hard facing. Of particular interest with respect to this invention are the aforementioned stellites preferably in the form of grindings. Typical weight compositions of such material are from about 10% to about 40% chromium, from about 10% to about 40% nickel, from about 5% to about 20% iron, from about 20% to about 60% tungsten, from about 0% to about 1% silicon, and the balance cobalt.

The material is digested in hydrochloric acid to form an aqueous acidic solution of essentially all of the starting cobalt in the form of cobalt chloride and the chloride salts of impurities as chromium, nickel and iron, and insoluble material which generally contains tungsten and silicon.

The hydrochloric acid is generally from about 6.0 to about 11.6 normal with from about 8.0 to about 11.0 normal being preferred. Temperature of digestion is generally from about 90° C. to about 105° C. with from about 95° C. to about 100° C. being preferred. Digestion times are generally from about 2 to about 10 hours with from about 4 to about 6 hours being preferred. Generally about 1 molar equivalents of cobalt are digested in about 5 molar equivalents of acid.

The solution is then separated from the insoluble material by any standard technique such as filtration.

It is desirable to oxidize the ferrous chloride in the acid digestion solution to ferric chloride. This is accomplished by adding hydrogen preoxide or bubbling air into the solution. Any iron not converted to ferric chloride will precipitate as ferrous oxalate in the subsequent precipitation step.

An oxalate producing compound, preferably oxalic acid or ammonium oxalate, is then added to the aqueous cobalt chloride acid digestion solution. Generally from about 1.0 to about 1.5 moles of oxalate per mole of cobalt is added. This amount insures that essentially all of the cobalt will be converted to cobalt oxalate. The oxalate treated solution is then adjusted to a pH of from about 1.5 to about 2.0 with a base, preferably sodium hydroxide. The resulting pH adjusted solution is preferably stirred for about 1 to 2 hours at about room temperature to allow for the formation of a first precipitate of cobalt oxalate that is substantially free of iron and chromium and a first mother liquor that contains essentially all of the iron and chromium. The precipitate contains at least about 99% of the cobalt that was in the acid solution. The first precipitate is then separated from the first mother liquor by any standard technique such as filtration.

The mother liquor can be treated with calcium hydroxide to precipitate the contained metals as their insoluble hydroxides.

The resulting cobalt oxalate is pure especially with respect to chromium. A typical weight analysis of the (dried) cobalt oxalate is as follows: 25% Co, 8.0% Ni, <1.0% Fe, <1.0% Cr.

The cobalt oxalate can now be processed to produce extra fine cobalt metal powder by known methods. A preferred method is disclosed in U.S. Pat. No. 4,329,169 entitled "Method For Producing Cobalt Metal Powder" dated May 11, 1982. That patent is hereby incorporated by reference.

Washing the cobalt oxalate by standard techniques, that is, with water, dilute acids or bases does not effectively reduce the levels of the contaminants found in the cobalt oxalate. The following method can be used to effectively purify the cobalt oxalate.

A solution of calcium chloride which is at a temperature of from about 95° C. to about 105° C. is added to the cobalt oxalate. This temperature is necessary because complete conversion of the cobalt oxalate to cobalt chloride does not take place at temperatures less than 95° C.

The calcium chloride solution contains from about 10 to about 14 moles of calcium chloride per liter. Generally about 0.5 moles of cobalt oxalate is added per mole of calcium chloride. This operation is done with agitation and agitation is carried out for about one hour. This insures the formation of a second precipitate which consists essentially of all calcium oxalate and essentially all of the impurities of the starting cobalt oxalate and a second mother liquor which contains at least about 98% of the cobalt as cobaltous chloride. A typical analysis of this cobaltous chloride liquor is as follows: 60 gpl Co, 10 gpl Ni, 0.05 gpl Fe, 0.005 gpl Cr.

Preferably after cooling to about 60° C., the second precipitate is separated from the second mother liquor by any standard technique such as filtration.

The cobaltous chloride is then converted to extrafine cobalt metal powder according to the process disclosed in U.S. Pat. No. 4,218,240, entitled Method for Producing Cobaltic Hexammine Compounds and Cobalt Metal Powder, issued Aug. 19, 1980. That patent is hereby incorporated by reference.

To more fully illustrate this invention, the following non-limiting examples are presented. All parts, portions, and percentages are on a weight basis, unless otherwise stated.

EXAMPLE 1

To a vessel equipped with a stirrer is added 100 parts of a stellite type grinding and about 400 parts of about 6 normal hydrochloric acid. The mixture is refluxed for about 6 hours and then filtered. Hydrogen peroxide is then added to the solution to oxidize the iron. Analysis of the filtrate showed the following:

59 g Co/l 17 g Cr/l 18 g Ni/l 5.5 g Fe/l

Oxalic acid is then added to the solution so that the mole ratio of oxalic acid to cobalt and nickel is about 1.5, sodium hydroxide is then added to adjust the pH to about 1.0. The resulting mixture is stirred for about one hour and then filtered. Analysis of the filtrate shows the following:

0.6 g Co/l 17 g Cr/l 0.08 g Ni/l 3.1 g Fe/l

A sample of the dried oxalate precipitate contains: 25% Co, 8.0% Ni, 0.35% Fe, and 0.06% Cr.

EXAMPLE 2

Cobaltous oxalate (about 27.0% cobalt) with the following impurities is used in the example below:

1% on a cobalt weight base—Fe, Mn, Ni, W, Na.
0.1–0.5% on a cobalt weight basis—Al, Cr, Mg, Ti.

In a beaker equipped with a magnetic stirring bar is added about 200 ml of water and about 94.4 g of $CaCl_2$. The mixture is then heated to about 100° C. and about 74 g of cobaltous oxalate is added and the mixture stirred for about one hour. The mixture is then cooled to about 60° C. and filtered to separate the resulting solution of cobaltous chloride from the resulting calcium oxalate precipitate. The precipitate is then washed and dried at about 100° C. for about 16 hours. Analysis of the dry solids shows about 0.26% cobalt. Analysis of the cobaltous chloride solution, shows about 80.8 g/l Co, and about 66 g/l Ca, a conversion of cobaltous oxalate to cobaltous chloride of about 99.5%. The cobaltchloride was then converted to extrafine cobalt metal powder. Analysis of the metal powder shows it to be greater than about 99.9% pure.

While there has been shown and described what are at present considered the preferred embodiments of the invention, it will be obvious to those skilled in the art that various changes and modifications may be made therein without departing from the scope of the invention as defined by the appended claims.

What is claimed is:

1. A process for recovering cobalt from an impure cobalt bearing material, said material having a composition of in percent by weight from about 10% to about 40% chromium, from about 10% to about 40% nickel, from about 5% to about 20% iron, from about 20% to about 60% tungsten, from about 0% to about 1% silicon, and the balance cobalt, said process comprising:
   (a) digesting said material in hydrochroric acid to form a solution containing essentially all of the cobalt values and the impurities of chromium nickel and iron and insoluble material containing the impurities of tungsten and silicon;
   (b) separating said solution from said insoluble material;
   (c) adding to said solution an oxalate producing compound in an amount sufficient to subsequently convert essentially all of the cobalt to cobalt oxalate;
   (d) adjusting the pH of the resulting oxalate treated solution with a base to from about 1.5 to about 2.0 to form a first precipitate which contains essentially all of the cobalt as cobalt oxalate and nickel impurities and a first mother liquor containing essentially all of the iron and chromium impurities of the solution; and
   (e) separating said first precipitate from said first mother liquor.

2. A process according to claim 1 wherein the impure cobalt bearing material is digested in hydrochloric acid of from about 6.0 to about 11.6 normal, at from about 90° to about 105° C., for from about 2 to about 10 hours.

3. A process according to claim 1 wherein the oxalate producing compound is selected from the group consisting of oxalic acid and ammonium oxalate.

4. A process according to claim 1 wherein from about 1.0 to about 1.5 moles of oxalate per mole of cobalt is added to the resulting solution of the hydrochloric acid digestion.

5. A process according to claim 1 wherein the base is sodium hydroxide.

6. A process according to claim 1 comprising the additional steps to further purify the cobalt:
   (a) adding to said first precipitate an aqueous solution of calcium chloride which is at a temperature of from about 95° to about 105° C. with agitation for a period of time sufficient to form a second precipitate which consists essentially of calcium oxalate and essentially all of the impurities of said first precipitate and a second mother liquor containing essentially all of the cobalt as cobalt chloride; and
   (b) separating said second precipitate from said second mother liquor.

7. A process according to claim 6 wherein the solution of calcium chloride contains from about 10 to about 14 moles of calcium chloride per liter of solution.

* * * * *